United States Patent [19]

Schuurs et al.

[11] E Patent Number: Re. 32,696

[45] Reissued Date of Patent: Jun. 14, 1988

[54] ENZYMATIC IMMUNOLOGICAL METHOD FOR DETERMINATION OF ANTIGENS AND ANTIBODIES

[75] Inventors: Antonius H. W. M. Schuurs; Bauke K. Van Weemen; Gerrit Wolters, all of Oss, Netherlands

[73] Assignee: Akzona Incorporated, Asheville, N.C.

[21] Appl. No.: 972,411

[22] Filed: Dec. 22, 1978

Related U.S. Patent Documents

Reissue of:

[64] Patent No.: 4,016,043
Issued: Apr. 5, 1977
Appl. No.: 610,469
Filed: Sep. 4, 1975

[51] Int. Cl.[4] ..... G01N 33/53; G01N 33/535; G01N 33/545

[52] U.S. Cl. ..... 435/7; 435/5; 435/810; 436/518; 436/531; 436/532; 436/808; 436/820

[58] Field of Search ..... 435/5, 7, 810; 436/518, 436/531, 532, 808, 820

[56] References Cited

U.S. PATENT DOCUMENTS

| | | | |
|---|---|---|---|
| Re. 29,169 | 4/1977 | Schuurs . | |
| 3,236,732 | 2/1966 | Arquilla . | |
| 3,293,146 | 12/1966 | Free . | |
| 3,293,147 | 12/1966 | Kosikowski . | |
| 3,472,738 | 10/1969 | Foster . | |
| 3,519,538 | 7/1970 | Messing . | |
| 3,555,143 | 1/1971 | Axen . | |
| 3,592,888 | 7/1971 | Wolf . | |
| 3,615,222 | 10/1971 | Mead . | |
| 3,639,558 | 2/1972 | Csizmas . | |
| 3,646,346 | 2/1972 | Catt . | |
| 3,652,761 | 3/1972 | Weetall . | |
| 3,654,090 | 4/1972 | Schuurs et al. . | |
| 3,700,609 | 10/1972 | Tregear et al. . | |
| 3,766,162 | 10/1973 | Spector . | |
| 3,775,536 | 11/1973 | Spector . | |
| 3,791,932 | 2/1974 | Schuurs et al. . | |
| 3,817,837 | 6/1974 | Rubenstein et al. . | |
| 3,826,619 | 7/1974 | Bratu . | |
| 3,839,153 | 10/1974 | Schuurs . | |
| 3,850,752 | 11/1974 | Schuurs . | |
| 3,852,157 | 12/1974 | Rubenstein et al. | 195/103.5 R |
| 3,867,517 | 2/1975 | Ling . | |
| 3,876,504 | 4/1975 | Koffler | 195/103.5 R |
| 3,879,262 | 4/1975 | Schuurs . | |
| 3,896,217 | 7/1975 | Johnson | 23/230 B |
| 3,896,218 | 7/1975 | Charm et al. . | |
| 3,905,767 | 9/1975 | Morris et al. | 195/103.5 R |
| 3,932,221 | 1/1976 | Pfleiderer . | |
| 3,935,074 | 1/1976 | Rubenstein . | |
| 3,951,748 | 4/1976 | Devlin . | |
| 4,002,532 | 1/1977 | Weltman . | |
| 4,016,043 | 4/1977 | Schuurs et al. . | |
| 4,154,795 | 5/1979 | Thorne | 422/102 |

FOREIGN PATENT DOCUMENTS

| | | |
|---|---|---|
| 7101728 | 2/1971 | Netherlands . |
| 1387625 | 3/1975 | United Kingdom . |

OTHER PUBLICATIONS

E. Haberman, Z. klin Chem. u. klin Biochem., 51–55, 8th Year, Jan. 1970.

W. J. Brzosko et al., The Lancet, 1058, May 16, 1970.

S. E. Salmon et al., The Journal of Immunology, 103, 129–137, Jul. 1969.

L. E. M. Miles and C. N. Hales, Nature, 219, 186–189 (Jul. 13, 1968).

(List continued on next page.)

*Primary Examiner*—Sidney Marantz
*Attorney, Agent, or Firm*—Wegner & Bretschneider

[57] ABSTRACT

The present invention relates, *inter alia,* to improvements in the sandwich technique for the determination of a component of an antigen-antibody reaction in a liquid sample to be tested, utilizing as reagents (a) one component of said reaction bound to the surface of a water-insoluble, water-insuspensible, solid carrier, and (b) a component having the same immunological properties covalently linked to an enzyme. *If and only if the component of the reagent that is water-insoluble and water-insuspensible has the same immunochemical properties as the component to be determined, is a predetermined amount of a binding partner for said first reagent (e.g., the reagent that is water-insoluble and water-insuspensible) added to the liquid sample.* The liquid sample is contacted and incubated with the reagent(s) to form a reaction mixture, the enzyme activity of either the liquid or solid phase of which is a measure of the presence and quantity of the component to be determined. The method is especially useful for diagnostic testing for hepatitis or rubella antibodies.

16 Claims, 1 Drawing Sheet

OTHER PUBLICATIONS

E. J. Ruitenberg, et al., "Serodiagnosis of *Trichinella spiralis* Infections in Pigs by Enzyme-linked Immunosorbent assays", Bull., Org. Mond. Sante 51 at 108-109 (1974).

A. H. W. M. Schuurs, et al., "Hapatitis B. Surface Antigen and Human Serum Proteins", Amer. J. Med. Sci., 270(1) at 173-177 (Mar. 19, 1975).

E. Engvall, et al., "Enzyme-linked Immunosorbent Assay, Elisa", from Symposium Protides of the Biological Fluids, Proceedings of the 19th Colloquium, 1971, at 553-556 (subsequently printed as Protides of the Biological Fluids", edited by H. Peeters, Pergamon Press, New York 1972).

"Viral Hepatitis", British Medical Bulletin, 28(2): pp. 138-141 (1972).

Clinica Chemica Acta 48: pp. 15-18 (1973).

"Enzyme-Linked Immunosorbent Assay, Elisa", Engvall et al., J. Immunology 109(1), 1972.

"A 'New' Antigen in Leukemia Sera", Blumberg et al., Jama 191(7): pp. 541-546.

"Medical Intelligence Current Concepts Australia Antigen and Hepatitis", Blumberg et al., New England J. Medicine 283(7): pp. 349-354 (1970).

"Recent Advances in our Understanding of Hepatitis Infections", Prince et al., Box Saagninis 24: pp. 8-16 (1973).

"Austrailia Antigen, Posttransfusion Hepatitis and the Chronic Carrier State", Sutnich et al., Amer. J. Dis. Child 123: pp. 392-400 (1972).

"Transfusion-Associated Hepatitis Not Due to Viral Hepatitis Type A or B", Feinstone et al., New England Journal of Medicine (1975).

"Enzyme-Labelled Immunoassays for Steroids", J. Landon et al., : pp. 183-188.

"Enzyme-Linked Immunosorbent Assay (Elisa) Quantitative Assay of Immunoglobulin 6", Engvall et al., Immunochemistray 8(9-1): pp. 871-874 (1971).

"Enzyme-Linked Immunosorbent Assay, Elisa", Engvall et al., J. Immunology 109: pp. 129-135 (1972).

"Enzyme Immunoassay (Eia) of Hepatitis B Surface Antigen", Wolters et al., A. Anal. Chem. Band 279(2): pp. 144 (1976).

"Solid-Phase Enzyme Immunoassay for Hepatitis B Surface Antigen", Robert Wei et al., Chem 23/5: pp. 813-815 (1977).

Catt et al., J. Lab. and Clin. Med., 70: pp. 820-822 (1967).

"Hepatitis B Virus Antigen: Validation and Immunologic Characterization of Low-Titer Serums with I-Antibody", C. M. Ling et al., 180 Science 203-205.

Belanger et al., Clin. Chem. Acta 48: 15-17 (1973).

Engvall et al., Biochem. Biophys. Acta 251: pp. 427-434 (1971).

Gradwohl's Clinical Laboratory Methods and Diagnosis, Frankel et al., 1970: pp. 355-358.

Habermann, "Ein Neues Prinzip zur Quantitativen Bestimmung Hochmolekularer Antigene (Verknupfungstest) und siene Anwendung auf Tetanustoxin, Serumalbumin and Ovalbumin", z. klin. Chem. u. clin. Biochem. 8, 51 (Jan. 1970).

Miles et al., "Labelled Antibodies and Immunological Assay System", Nature, 219: pp. 186 (Jul. 13, 1968).

Miles et al., "The Use of Labelled Antibodies in the Assay of Polypeptide Hormones", J. Nucl. Biol. Med., 13: p. 10 (1969).

Berson et al., "Radioimmunoassay of Acth in Plasma", J. Clin. Invest. 47: p. 2725 (1968).

Catt et al., "Solid-Phase Radioimmunoassay in Antibody-Coated Tubes", Science 158: p. 1570 (1967).

Hales et al., "Immunoassay of Insulin with Insulin-Antobidy Precipitate", Biochem J. 88: p. 137 (1963).

Gerloff et al., "Precipitation of Radio-labelled Poliovirus with Specific Antibody and Antiglobulin", J. Immunology 89: p. 559 (1962).

Kirkham et al. (editor), Radioimmunoassay Methods, pp. 405-488 (1971).

Kirkham et al. (editor), "Solid Phase Antigen-Antibody Systems, a paper by Wide reprinted in the Kirkham et al. book; Radioimmunoassay Methods, pp. 405-412.

Kirkham et al. (editor), "Untitled conference discussion reported in the Kirham et al., book Radioimmunoassay Methods, pp. 481-488; the conference was held in Edinburgh, Scotland in Sep. 1970.

Boyer (editor); Annual Review of Biochemistry, vol. 35: part II, p. 902 (1966).

Midgley, "Radioimmunoassay: A Method for Human Chorionic Gonadotropin and Human Luteinizing Hormone", Endocrinology 79: p. 10 (1966).

Midgley et al., "Radioimmunoassays Employing Double Antibody Techniques Karolinska Symposia", Acta Endocr. (KPH.) Suppl. 142: p. 247 (1969).

Midgley et al., "Radioimmunoassay of Steroids Karolinska Sy mposia II", Acta Endocr. (KPH.) Suppl. 147: p. 320 (1970).

Miles et al., "Labelled Antobidies and Immunological Assay Systems", Nature 219: p. 186 (1968).
Miles et al., "The Use of Labelled Antibodies in the Assay of Polypeptide Hormones", J. Nucl. Biol. Med. 13: p. 10 (1969).
Miles et al., "Immunoradiometric Assay of Human Growth Hormone", Lancet 2: pp. 492-293 (8/31/68).
Salmon et al., "'Sandwich' Solid Phase Radioimmunoassay for the Quantitative Determination of Human Immunoglobulins", J. Immunology 103: p. 129 (1969).
Spector et al., "Morphine: Radioimmunoassay", Science 168: p. 1347 (1970).
Walsh et al., "Detection of Australia Antigen and Antibody by Means of Radioimmunoassay Techniques", J. Infectious Diseases 121: p. 550 (1970).
Wide et al., "Radio Immunoassay of Proteins with the use of Sephadex-Coupled antibodies", Biochem. Biophys. Acta 130: p. 257 (1966).
Wide et al., "Diagnosis of Allergy by An In-Vitro Test for Allergen Antibodies", Lancet 2: pp. 1105-1107 (11/25/67).
Wide, "Early Diagnosis of Pregnancy", Lancet, pp. 863-864 (10/25/69).
Wide, "Radioimmunoassays Employing Immunosorbents", Acta Endocr. (KPH.) Suppl., 142: p. 207 (1969).
Yalow et al., "Immunoassay of Endogenous Plasma Insulin in Man", J. Clin. Invest. 39: p. 1157 (1960).
Cuatrecasas, "Protein Purification by Affinity Chromatography", J. Biol. Chem. 245: p. 3059 (1970).
Cuatrecasas et al., "Selective Enzyme Purification by Affinity Chromatography", Proc. Nat. Acad. Sci. Bio. Chemistry 61: p. 636 (1968).
Nakane et al., "Enzyme-Labelled Antibodies: Preparation and Application for the Localization of Antigens", J. Histochem. Cytochem. 14: p. 929 (1967).
Nakane et al., "Enzyme-Labelled Antibodies for the Light and Electron Microscopic Localization of Tissue Antigens", J. of Cell. Biol. 33: 307 (1967).
Porath et al., "Chemical Coupling of Protins to Agarose", Nature 215: 1491 (1967).
Axen et al., "Chemical Coupling of Peptides and Proteins to Polysaccharides by Means of Cyanogen Halides", Nature 214: p. 1302 (1967).
Boyer (editor), Annual Review of Biochemistry, vol. 35, part II, p. 902 (1966).
Miles et al., "The Preparation and Properties of Purified 125 I-Labelled Antibodies to Insulin", Biochem. J. 108: p. 611 91968).
Avrameas et al. "Method of Marking Antigens and Antibodies with Enzymes and its application in Immunodiffusion", C. R. Acad. Sc. Paris, t. 262 (6/13/66) Series D-2543, Biochime.
Goke et al., "Hepatitis Antigen", The Lancet 2: p. 7605 (5/31/69).
Avrameas, "Detection of Antibodies and Antigen with the Aid of Enzymes", Bull. Soc. Chem. Biol. 50: p. 1169 (1968).
Avrameas, "Coupling of Enzymes to Proteins with Glutaraldehyde", Immunochemistry 6: p. 43 (1969).
Avrameas et al., "The Cross-Linking of Proteins with Glutaraldehyde and its Use for the Preparation of Immunoabsorbents", Immunochemistry 6: p. 53 (1969).
Sternberger et al., "The Unlabelled Antibody Enzyme Method of Immunohistochemistry", J. Histochem Cycochem 18: 315 (1970).
Avrameas, "Immunoenzyme Techniques: Enzymes as Markers for the Localization of Antigens and Antibodies", Int'l. Rev. Cytol. 27: p. 349 (1970).
Ostrowski et al., "Autoradiographic Detection of Antigens in Cells Using Tritium-Labelled Antibodies", J. Histochem. Cytochem 18: p. 490 (1970).
Engvall et al., "Enzyme Linked Immunosorbent Assay, II. Quantitative Assay of Protein Antigen, Immunoglobulin by Means of Enzyme-Labelled Antigen and Antibody-Coated Tubes", Biochem. Biphy. Acta 251: 427-434 (Jul. 1971).
Engvall et al., "Enzyme-Linked Immunosorbent" Elisa) Quantitative assay of Immunoglobulin G", Immunochemistry 8: pp. 871-874 (1971).
Van Weemen et al., "Immunoassay Using Antigen-Enzyme Conjugates", Febs Lett 15(3): pp. 232-236 (1971).
Rosenthal et al., "Rapid Micro-Radioimmunoassay for the Measurement of Antiviral Antibody", J. Immunology 109(1): pp. 171-173 (1972).
Hutchinson et al., "Simplified Radioimmunoassay for Diagnostic Serology", Applied Microbiology 24(2): pp. 742-849 (1972).
Belanger et al., "Enzyme-Linked Immunoassay for Alpha-Fetoprotein by Competitive and Sandwich Procedures", Clinica Chemica Acta 48: pp. 15-18 (1973).
Ishikawa et al., "Enzyme-Immunoassay of Insulin by Fluorimetry of the Insulin-glucoamylase Complex", J. Biochemistry 73: pp. 1319-1321 (1973).
Habermann, "New Developments in the Detection of Bacterial and Viral Antigens and Their Antibodies", Report to Int'l. Atomic Energy Agency, Vienna, 1973.
Nakane et al., "Peroxidase-Labelled Antibody-A New Method of Conjugation", J. Histochemistry and Cytochemistry 22(12): pp. 1084-1091 (1974).
Pesce et al., "Use of Enzyme-Linked Antibodies to Measure Serum Anti-DNA Antibody of Septemic Lupus Erythematosus", Clin. Chem., 20(3): p. 353 (1974).

Voller et al., "A Microplate Method of Enzyme-Linked Immunosorbent Assay and Its Application to Malaria", Bulletin of the World Health Organization 51: pp. 209-211, (1974).

"Dynatech Microelisa System" (brochure, prior to May 28, 1975).

"Hepatitus Scientific Memorandum", Calspan Corp., Buffalo, N.Y. (1975).

Wolters et al., "Letter to the Editor" 'Enzyme-Immunoassay (EIA) for HBsAg in Microtitre Plates'", Lancet (1975).

Simon, "The Methoden Des Klinish Chemischen Laboratoriums", Medizinishe Monatsschrift 30: pp. 518-520 (1976).

Bout et al., "Immunodiagnosis of Human Parasitic Diseases by Elisa", Proceedings of the First International Symposium on Immunoenzymatic Techniques, Paris, 2-4 Apr. 1975, No. 2, Institut National De La Sante Et De La Recherch Medicale (1976), pp. 175-182.

Engvall et al., "Enzyme-Linked Immunosorbent Assay, Elisa", Proceedings of the First International Symposium on Immunoenzymatic Techniques, Paris, 2-4 Apr. 1975, No. 2, Institut National De La Sante Et De La Recherch Medicale (1976), pp. 135-147.

Voller et al., "The Application of Micro-Plate Enzyme-Linked Immunosorbent Assays to Some Infectious Diseases", Proceedings of the First International Symposium on Immunoenzymatic Techniques, Paris, 2-4 Apr. 1975, No. 2, Institut National De La Sante Et De La Recherch Medicale (1976), pp. 167-173.

Van Weemen et al., "Sensitivity and Specificity of Hapten Enzyme-Immunoassays" Proceedings of the First International Symposium on Immunoenzymatic Techniques, Paris, 2-4 Apr. 1975, No. 2, Institut National De La Sante Et De La Recherch Medicale (1976), pp. 125-133.

M. J. Evans and D. S. Yohn, J. Immunol., 104(5), p. 1132 (May 1976).

D. E. Bidwell et al., "The Enzyme-Linked Immunosorbent Assay (Elisa)", Bull. World Health 54: p. 129 (1976).

G. Brian Wisdom, "Enzyme-Immunoassay", Clin. Chem. 22/8: pp. 1243-1245 (1976).

J. H. Kennedy et al., "Protein-Protein Coupling Reactions and the Applications of Protein Conjugates", Chimica Clinica Acta 70: pp. 1-29 (1976).

A. Voller et al., "Manual of Clinical Immunology Ch. 69: p. 506 (1976).

K. W. Walls et al., "Use of the Enzyme-Linked Immunosorbent Assay (EIA) and its Micro-Adaptation for the Serodiagnosis of Toxoplasmosis", J. Clinical Microbiology 5(3): pp. 273-277 (1977).

R. H. Yolken, "Enzyme-Linked Immunosorbent Assay (Elisa) for Detection of Human Reovirus-Like Agent of Infantile Gastroenteritis, The Lancet (Aug. 6, 1977).

M. F. Clark et al., "Characteristics of the Microplate Methods of Enzyme-Linked Immunosorbent Assay for the Detection of Plant Viruses", J. Gen. Virol., 34: pp. 475-483 (1977).

J. Kalmakoff et al., "Solid Phase Radioimmunoassays Using Labeled Antibodies: A Conceptual Framework for Designing Assays", J. Immunological Methods 14: pp. 73-84 (1977).

G. Wolters et al., "Enzyme-Linked Immunosorbent Assay for Hepatitis B Surface Antigen", 1 J. Infect. Diseases, vol. 136, Supp. 5311 (1977).

"Digoxin Radioimmunoassay Dealing with a Loss of Sensitivity", Clin. Chem. vol. 19, p. 688 (1973).

"Pitfalls in Iodine-125 Digoxin Measurement", R. Ravel Co-author, Annals of Clin. and Lab. Sci., vol. 6, p. 365 (1976).

Lancet, May 1970, p. 1057.

Nature, Feb. 23, 1976, p. 825.

FEBS Letters, vol. 47(1), Oct. 1974, "An Immunoassay for a Pregnancy Associated 2-Macroglobulin Using Antibody-Enzyme Conjugates", Stimson et al.

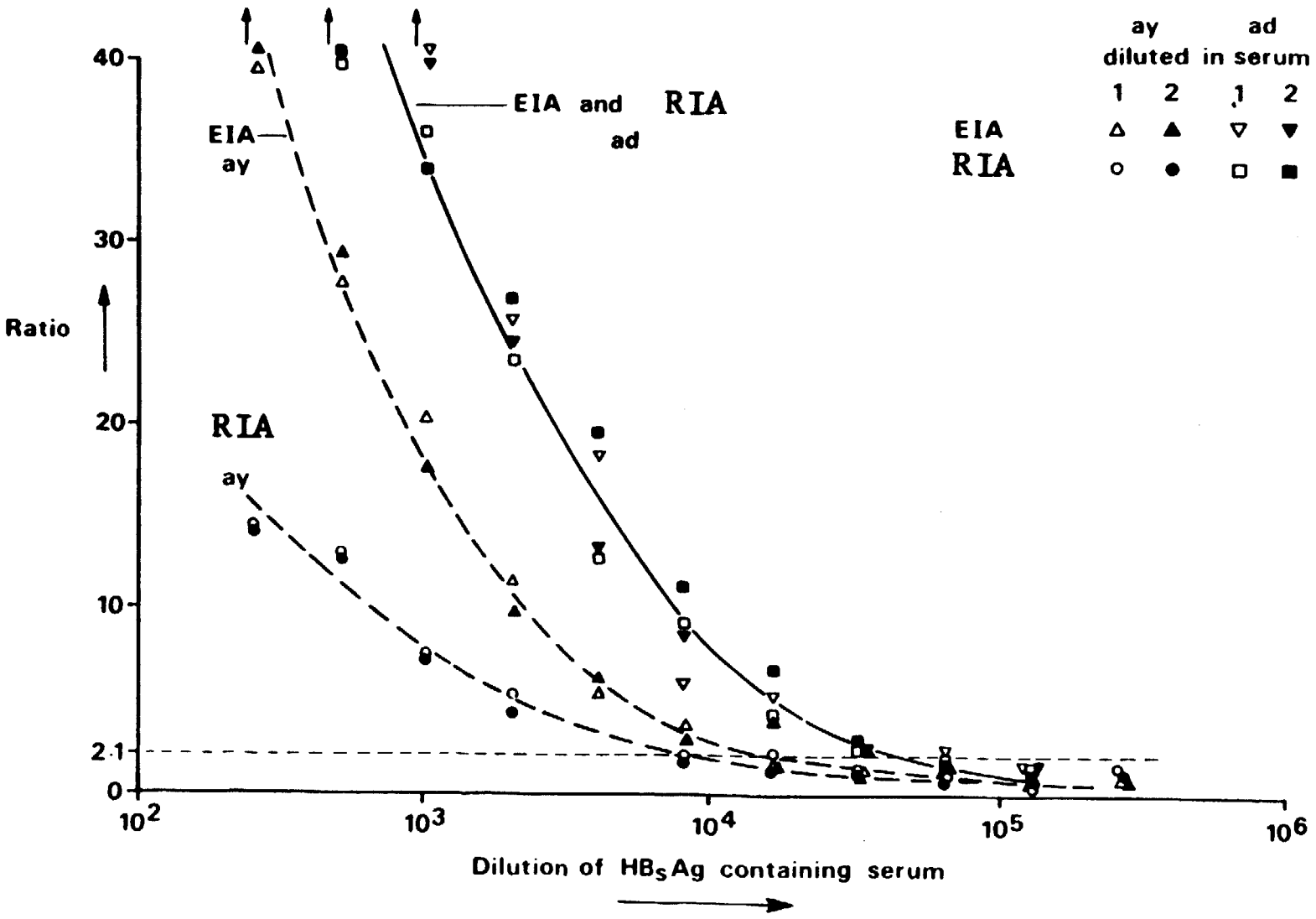
ay
ad
diluted in serum
1 2
1 2
EIA
RIA
EIA and RIA
ad
EIA
ay
RIA
ay
Ratio
40
30
20
10
2.1
0
$10^2$
$10^3$
$10^4$
$10^5$
$10^6$
Dilution of $HB_sAg$ containing serum

ENZYMATIC IMMUNOLOGICAL METHOD FOR DETERMINATION OF ANTIGENS AND ANTIBODIES

Matter enclosed in heavy brackets [ ] appears in the original patent but forms no part of this reissue specification; matter printed in italics indicates the additions made by reissue.

BACKGROUND OF THE INVENTION

This invention relates to a diagnostic method for the [direction] *detection* and determination of antigens and antibodies. More particularly, this invention relates to diagnostic methods for the detection and determination of pathogenic disease antigens and antibodies, such as hepatitis and rubella antigens and their associated antibodies.

A number of immunological methods have been developed for the determination of antigens and antibodies, including methods for the determination of hepatitis B surface antigen ($HB_2Ag$), a component of hepatitis B virus and its associated antibodies.

In this field it is important that whatever methods are used are as sensitive and reliable as possible since an incorrect diagnosis can have serious consequences. This is especially true of the determination of hepatitis antigens and their associated antibodies since the transmission of the hepatitis virus via blood donors constitutes a significant public health risk.

Up to the present time, the radio-immunoassay (RIA) method in its various forms has been the most sensitive system available. This method has several disadvantages, however, including the requirement of special equipment, trained staff, the need for extra safety measures to protect against harmful radiation, and the short half-life span of the radioactive labelling element. The possibility of replacing the radioactive label with an enzyme label was proposed in 1968 in an article by L. E. M. Miles and C. N. Hales, entitled "Labelled Antibodies and Immunological Assay Systems," Lancet, London 1968 II, page 492; Nature, Vol. 219, pages 186–189 (July 13, 1968), but no procedural details were provided, the article failing to offer more than the general idea, leaving it to future workers to determine the basic steps and to perform the extensive experimentation needed to establish a practical operative enzymic immunoassay method.

The pioneering work on enzyme-immunoassay (EIA) methodology was performed by Schuurs and coworkers, and is disclosed in a series of their U.S. Pat. Nos. 3,654,090, 3,791,932, 3,850,752, 3,839,153, and 3,879,262.

In the course of the further evolution of the radio-immunoassay procedures by numerous workers, it was pointed out out in an article by E. Habermann, entitled "A new Principle for the Quantitative Determination of High Molecular Antigens (Junction Test), etc." published in Z. klin. Chem. u. klin. Biochem., 8th year, January, 1970, pages 51–55, that those methods based on the competition of radio-labelled and unlabelled antigens for a limited amount of antibodies gave better results than other methods.

The Habermann article proposed an RIA method [in] which [in a first step,] *involved reacting an unknown bindable substance with an insolubilized binding partner to insolubilized the unknown. The insolubilized unknown was then, in turn, reacted with a radioactively*

*labelled binding partner, and the quantity of insolubilized radioactivity determined. More specifically, Habermann proposed an RIA method whereby* the antigen is adsorbed on an antibody fixed with a covalent bond by a solid phase, e.g., celluose; a second step consists [in] *of* fixing [by] labelled antibodies *to* those antigen determinants remaining accessible. The non-fixed component of the antibody preparation is removed by washing. The radioactivity of the solid phase is correlated with the antigen content of the original solution. Since the labelled and solid phase antibodies are joined via the antigen, the author called the technique the "junction test." This arrangement is also known in the art as the "sandwich technique or method." The Habermann article, referred to the earlier suggestion of Miles and Hales (loc. cit.), and contained a passing suggestion that the test could be improved in sensitivity by coupling the antibody molecule with an easily detectable enzyme, but also offered no further suggestions, leaving it to others to develop such an enzyme method. *Haberman does not set forth any specific assay employing enzymes. Apart from the general statement referred to above, Habermann merely cites a supposed suggestion by Miles et al about how to use enzymes—but the referenced Miles et al article contains no mention of enzymes.*

In Schuurs et al. U.S. Pat. No. 3,791,932, there is disclosed, in Example III, [a rudimentary] *first-generation* sandwich-type procedure for the determination of human chorionic gonadotropin (HCG) and luteinizing hormone (LH) in low concentrations by means of an enzyme-antibody coupling component, in accordance with which a predetermined amount of [HCG] *anti-HCG* is first coupled to a solid immuno-adsorbent (m-aminobenzyloxymethyl cellulose). [Antibodies] *Purified Antibodies* from rabbit anti-HCG serum are then coupled to an enzyme (horse radish peroxidase, HRP) [and the coupling product is bound to HCG cellulose]. *The test proceeds when an* HCG [and] *or* LH dilution series [are] *is* mixed with anti-HCG cellulose [to form an immunoadsorbent, to which] *immunoadsorbent forming an antigen-antibody complex. Then* a given amount of the antibody-enzyme coupling product is added, and the enzyme activity of the supernatant liquid is determined. This procedure is somewhat involved and requires a number of coordinated operating steps.

It is an object of the present invention to develop and further improve and simplify the early version of the sandwich technique as applied to the determination of antigens and antibodies.

*It is an object of the present invention to use a water-insoluble, water-insuspenssible solid carrier for binding one component of an antigen-antibody reaction.*

*It is another object of the present invention to provide a technique for the determination of antigens and antibodies that has sensitivity as good as the prior art RIA methods.*

GENERAL DESCRIPTION OF THE INVENTION

In accordance with the present invention, there is provided a novel, very simple and sensitive enzyme immunoassay (EIA) test system especially adapted for the detection and determination of a component of an antigen-antibody reaction. The general principle of the procedure of the invention is that of employing as a test reagent a given amount of one component of said reaction bound to the surface of a water-insoluble, water-insuspensible solid carrier, and as a second reagent, a given amount of the same component covalently linked to an enzyme. The liquid sample containing the component to be determined is contacted with these reagents. In case the component to be determined and the component bound to the solid carrier are the same, a given amount of a binding partner of said component is added to the liquid sample. Upon mixing the reagents and the sample, there is formed a reaction mixture having a solid phase and a liquid phase. Finally the enzyme activity of the solid or liquid phase is determined, said activity being a measure of the presence and quantity of the component to be determined.

The enzyme-immunoassay (EIA) method according to the present invention does not possess the disadvantages of a radioimmunoassay method, and is simpler to set up and perform than the earlier EIA methods, but, surprisingly, is as sensitive as the RIA method. One of the advantages of the EIA according to the present invention is that by using an enzyme as a labelling means the immunological reaction can be measured by a color reaction. Either a colored substrate or a colored end-product should participate in the enzyme-catalyzed reaction so that the detection can take place by reading with the naked eye or by measurement of the extinction.

More specifically, the method of the present invention comprises contacting a liquid sample, for example serum or plasma, containing an unknown amount of antigen or antibody, with a predetermined amount of either the [antigen] *antibody* or the [antibody], *antigen respectively,* which is bound to the surface of a water-insoluble, water-insuspensible, solid carrier. The liquid sample is then incubated with this coated solid carrier for a period of 0.5 to 35 hours, usually at a temperature between 4° and 50° C. After aspiration and washing, the foregoing solid phase is contacted with an amount of the same component covalently linked to an enzyme. If the component to be determined in the liquid sample, and the component coupled to the solid carrier are the same, the solid phase is contacted with a binding partner for the component to be determined.

The binding partner is employed in an insoluble form. The determination can take place by adding the binding partner in an insoluble form, or it can be added in a dissolved form, and insolubilized afterwards. The binding partner is preferably a protein capable of binding the antigen or antibody specifically.

After an incubation period, usually from 0.5 to 25 hours, and at a temperature between 4° and 50° C., aspiration and washing, the enzymatic activity bound to the solid phase is determined, which activity is a measure of the pressure of the antigen or antibody component in the liquid sample tested.

Both for the detection and quantitative determination of the antigen or antibody, the foregoing reagents are employed in predetermined amounts.

The solid carrier to which one of the components is bound may be any water-insoluble, water-insuspensible, solid carrier. Examples of suitable solid carriers include large beads, e.g., of polystyrene, filter paper, test tubes, and microtiter plates. The immunological component may be bound to the solid carrier by covalent bonds or by adsorption. The advantage of the use of a solid carrier is that no centrifugation step is needed for the separation of solid and liquid phase.

As a solid carrier, use is preferably made of a test tube of a microtiter plate the inner walls of which are coated with the immunological component.

The antigen or antibody enzyme conjugate consists of the immunological component covalently linked to one or more enzyme molecules. Such linking can be achieved either by direct condensation or by using external bridging molecules, in accordance with methods known to those skilled in the art.

Thus, the production of enzyme coupling products employing a covalent bond can be effected by reagents such as carbodiimides, diisocyanates, glutaric aldehyde, and bis-diazobenzidine.

The choice of the enzyme that is to form a part of the coupling product is determined by properties such as the specific binding activity (a high conversion rate increases the sensitivity of the test system) and the simplicity of determination of the enzyme. The determination of an enzyme catalyzing a conversion in which colored reaction components are involved, is simple. Such colorimetric determinations can be automatic in a simple manner. It is also possible to employ enzymes catalyzing those conversions in which reaction components are involved that can be determined spectrophotometrically or fluorimetrically. These determinations are also suitable for automation, which is an additional advantage.

As enzymes suitable for the method of the invention there can be employed catalase, peroxidase, urease, glucose oxidase, alkaline phosphatase. Horse radish peroxidase is preferred.

The method according to the present invention can be used for the detection and determination of antigens and antibodies in general, including bacteria, viruses, hormones, proteins and their associated antibodies, but is particularly suited for the detection and determination of hepatitis B surface antigen and rubella and their associated antibodies. The invention will be illustrated with respect to these examples but is not to be considered as limited thereto.

In order to compare the enzyme-immunoassay of the invention with the corresponding radio-immunoassay, for the detection of $HB_SAg$, two $HB_SAg$-containing sera (1 subtype ad, 1 subtype ay) were taken and were diluted in two different normal sera, free from $HB_SAg$ and anti-$HB_S$. The results from these four dilution series are indicated in the accompanying drawing. They demonstrate that EIA and RIA have about the same sensitivity, but that the EIA gives a steeper dose-response curve with the serum containing subtype ay.

The enzyme immunoassay for $HB_SAg$ according to the present invention detected all antigen-positive samples "A," "B" and "C" of the NIH reference panel No. 2, both by eye reading and extinction measurement. This means that the assay system according to the present invention has at least "third generation" sensitivity as defined in the Federal Register, Vol. 39, No. 132, of July 9, 1974.

DESCRIPTION OF THE PREFERRED EMBODIMENTS

The following examples serve to illustrate the practice of the invention, but are not to be regarded as limiting:

EXAMPLE I

Detection of Hepatitis B Surface Antigen In Human Serum or Plasma 0.1 ml test sample (human serum or plasma) is added to each well of a polystyrene microtiter plate to the inner walls of which sheep anti-(Hepatitis B surface antigen) is bound. The plate is incubated for 2 hours at 37° C. The wells are emptied by aspiration. Each well is washed three times with 0.2 ml 0.2 M TRIS (trihydroxy-methylaminomethane; 2-amino-2-hydroxymethyl-1,3-propanediol) buffer, pH 7.4 (buffer A). 0.1 ml Horse radish peroxidase coupled to sheep anti-(Hepatitis B surface antigen) in a predetermined dilution in Buffer A is added. The plate is incubated for 2 hours at 37° C. The wells are emptied by aspiration. Each well is washed four times with 0.2 ml buffer A. 0.1 ml of a substrate solution of:

0.4 mg orthophenylene diamine per ml 0.2 mg urea-peroxidase per ml in a McIlvain buffer of pH 5.0. is added to each well. The plate is incubated for 60 minutes at room temperature. The reaction is stopped by adding 0.05 ml of 0.5 N sulphuric acid. The color is read by eye or measured colorimetrically at 492 nm.

A result is called positive if the ratio is ≧2.1, i.e., the average extinction is at least 2.1 times the average extinction of six negative control sera.

Result A

Titration of two Hepatitis B surface antigen-positive sera of the ay and ad subtypes in enzyme immunoassay and a radio-immunoassay licensed by the U.S. Federal Drug Administration. The positive sera were diluted in two sera negative for Hepatitis B surface antigen and for anti-(Hepatitis B surface antigen), so that the serum concentration was the same in all dilutions. The curves of the ad subtype in both tests are represented by one line. (See accompanying drawing).

Result B

Reaction of the NIH Reference panel No. 2 in the abovementioned assay system.

| lot No. | ratio | eye-reading | lot No. | ratio | eye-reading |
|---|---|---|---|---|---|
| 201 | >26. | + | 229 | 1.51 | − |
| 202 | >26. | + | 230 | 1.72 | − |
| 203 | 0.97 | − | 231 | 1.51 | − |
| 204 | 10.33 | + | 232 | >26. | + |
| 205 | >26. | + | 233 | 1.15 | − |
| 206 | >26. | + | 234 | >26. | + |
| 207 | 1.79 | − | 235 | >26. | + |
| 208 | >26. | + | 236 | 1.56 | − |
| 209 | >26. | + | 237 | 1.16 | − |
| 210 | >26. | + | 238 | >26. | + |
| 211 | 1.11 | − | 239 | >26. | + |
| 212 | 1.25 | − | 240 | 1.39 | − |
| 213 | >26. | + | 241 | 1.38 | − |
| 214 | >26. | + | 242 | 1.23 | − |
| 215 | 2.05 | − | 243 | >26. | + |
| 216 | 1.32 | − | 244 | >26. | + |
| 217 | >26. | + | 250 | >26. | + |
| 218 | >26. | + | 251 | >26. | + |
| 219 | >26. | + | 252 | >26. | + |
| 220 | >26. | + | 253 | >26. | + |
| 224 | 1.04 | − | 254 | >26. | + |

-continued

| lot No. | ratio | eye-reading | lot No. | ratio | eye-reading |
|---|---|---|---|---|---|
| 225 | 1.16 | − | 255 | >26. | + |
| 226 | >26. | + | 256 | >26. | + |
| 227 | 1.36 | − | 260 | >26. | + |
| 228 | >26. | + | 261 | >26. | + |

EXAMPLE II

Detection of antibodies against hepatitis B surface antigen in human serum of plasma 0.1 ml test sample (human serum or plasma) is added to each well of a polystyrene microtiter plate to the inner walls of which sheep anti-(Hepatitis B surface antigen) is bound. 0.05 ml of a predetermined dilution of hepatitis B surface antigen in 0.2 M TRIS buffer pH 7.4 is added to each well. The plate is incubated for 2 hours at 37° C. and treated further in the same way as in Example 1.

Results

Extinction after testing a dilution series of an anti-(hepatitis B surface antigen)-containing serum in antigen-and antibody-negative serum and six antigen- and antibody-negative control sera. Serum positive for anti-(Hepatitis B surface antigen)

| Undiluted | 1/2 | 1/4 | 1/8 | 1/16 | 1/32 | 1/64 | 1/128 | 1/256 | 1/512 |
|---|---|---|---|---|---|---|---|---|---|
| 0.050 | 0.051 | 0.049 | 0.062 | 0.060 | 0.058 | 0.168 | 0.200 | 0.203 | 0.198 |

Negative control sera undiluted: serum No.

| 1 | 2 | 3 | 4 | 5 | 6 |
|---|---|---|---|---|---|
| 0.201 | 0.197 | 0.232 | 0.205 | 0.212 | 0.218 |

A reaction is called positive is the extinction is ≦50% of the average extinction of 6 negative control sera.

EXAMPLE III

Detection of antibodies against Rubella virus in human serum or plasma 0.5 ml of test sample (human serum or plasma) is added to polystyrene tubes $\phi$ 1 cm to the inner walls of which inactivated Rubella virus is coupled. The tubes are incubated for 1 hour at 37° C. The tubes are emptied by aspiration. Each tube is washed three times with 2 ml 0.15 M phosphate buffer. 0.5 ml horse radish peroxidase coupled to inactivated Rubella virus in a predetermined dilution in 0.2 M TRIS buffer +0.1% triton $X_{100}$ is added. The tubes are incubated for 3 hours at 37° C. Each tube is washed three times with 2 ml 0.2 M TRIS buffer+0.1% triton $X_{100}$. The horse radish peroxidase activity is determined by adding 0.5 ml substrate solution (see example I) and incubating for 60 minutes at 37° C. The reaction is stopped by adding 0.25 ml of 0.5 N sulphuric acid. The color is measured colorimetrically at 494 nm. A result is called positive if the ratio is ≧2.9, i.e., the average extinction is at least 2.9 times the average extinction of 8 negative control sera.

Results

Extinction after testing a dilution series of an anti-(Rubella-virus)-containing serum in serum negative for Rubella virus and anti-(rubella virus), and eight negative control sera. Serum positive for anti-rubella-virus:

| 1/32 | 1/64 | 1/128 | 1/256 | 1/512 | 1/1024 | 1/2048 | 1/4096 | 1/8192 | 1/6384 |
|---|---|---|---|---|---|---|---|---|---|

-continued

| | | | | | | | | | |
|---|---|---|---|---|---|---|---|---|---|
| >2.000 | >2.000 | >2.000 | 1.653 | 0.985 | 0.499 | 0.285 | 0.175 | 0.103 | 0.095 |

Negative control sera undiluted:

| serum No. | | | | | | | |
|---|---|---|---|---|---|---|---|
| 1 | 2 | 3 | 4 | 5 | 6 | 7 | 8 |
| 0.058 | 0.092 | 0.070 | 0.101 | 0.085 | 0.063 | 0.058 | 0.082 |

EXAMPLE IV

Detection of rubella virus in human serum or plasma 0.5 ml of test sample (human serum or plasma) is added to 0.1 ml of a predetermined solution of rabbit anti-rubella-virus. The mixture is incubated for 1 hour at 37° C. 0.5 ml of this mixture is added to a polystyrene tube $\phi$1 cm to the inner walls of which inactivated rubella virus is bound. The tubes are incubated for 1 hour at 37° C. and treated further inthe same way as in Example III.

Results

Extinctions after testing a dilution series of a rubella virus-containing serum in serum negative for rubella-virus and anti-rubella-virus. Serum positive for rubella virus:

| 1/100 | 1/200 | 1/400 | 1/800 | 1/1600 | 1/3200 | 1/6400 | 1/12800 | 1/25600 |
|---|---|---|---|---|---|---|---|---|
| 0.075 | 0.076 | 0.073 | 0.090 | 0.088 | 0.097 | 0.201 | 0.252 | 0.0249 |

Negative control sera undiluted:

| serum No. | | | | | | | |
|---|---|---|---|---|---|---|---|
| 1 | 2 | 3 | 4 | 5 | 6 | 7 | 8 |
| 0.250 | 0.238 | 0.278 | 0.275 | 0.263 | 0.291 | 0.0258 | 0.261 |

A reaction is called positive if the extinction is $\leqq$50% of the average extinction of 8 negative control sera.

For the performance of the method according to the invention, a test pack or kit of the reagents is preferably employed, chiefly composed of:

a. a given quantity of a component of the antigen-antibody reaction bound to a water-insoluble, water-insuspensible solid carrier;

b. a substance having the same immunological properties as said component, covalently linked to an enzyme;

c. the binding partner of the component to be determined if the component has the same immunological properties as the component in (a). According to their nature, these reagents can be preserved by freeze-drying or dissolved in a buffer. Thus, a specific test pack may comprise (a) the antibody against hepatitis B surface antigen coupled to a water-insoluble, water-insuspensible, solid carrier; (b) said antibody covalently linked to an enzyme; and (c) hepatitis B surface antigen in case the component to be determined is the antibody against hepatitis antigen.

What is claimed is:

[1. A method for the detection and determination of a component of an antigen-antibody reaction in a liquid sample containing the component to be determined, comprising the steps of:

a. providing a given quantity of a first reagent consisting of one component of said reaction selected from the group consisting of an antigen and an antibody bound to the surface of a water-insoluble, water-insuspensible, solid carrier;

b. providing a given amount of a second reagent consisting of a component having the same immunological properties as the component in the said first reagent covalently linked to an enzyme, and also providing a predetermined amount of the binding partner for the component to be determined, when the component in said liquid sample and the component bound to said solid carrier have the same immuno-chemical properties;

c. contacting a given quantity of said liquid sample with said reagents forming a reaction mixture having a solid phase and a liquid phase; and d. determining the enzyme activity of either the solid or the liquid phase which is a measure of the presence and quantity of the component to be determined.]

[2. A method for determining the presence of a component of an antigen-antibody reaction in a liquid sample containing the component to be determined comprising the steps of:

a. providing a given quantity of a first reagent consisting of one component of said reaction selected from the group consisting of an antigen and an antibody bound to the surface of water-insoluble, water-insuspensible, solid carrier, and also providing a predetermined amount of the binding partner for the component to be determined when the component in said liquid sample and the component bound to said solid carrier have the same immuno-chemical properties;

b. contacting and incubating a given quantity of said liquid sample with said first reagent;

c. washing said solid carrier;

d. providing a given quantity of a substance having the same immunological properties as the component previously bound to the solid carrier, said substance being covalently linked to an enzyme;

e. contacting and incubating the solid phase from step (c) with said enzyme-linked substance;

f. washing the solid carrer; and g. determining the enzyme activity substance bound to the solid phase, which is a measure of the presence and quantity of the component to be determined.]

[3. The method of claim 2 wherein said liquid sample and the binding partner of the component to be determined are preincubated with each other, before contacting the sample with said solid carrier.]

[4. A method for the detection and determination of a component in the reaction of a hepatitis antigen and the associated antibody in a liquid sample containing said component, comprising the steps of:

a. providing a given quantity of a reagent consisting of one component of said reaction selected from the group consisting of said antigen and said antibody bound to a water-insoluble, water-insuspensible, solid carrier;

b. contacting and incubating said liquid sample with said solid carrier of step (a) to form a reaction mixture;

c. providing a given quantity of a substance having the same immunological properties as the component bound to said solid carrier, said substance being covalently linked to an enzyme, and also providing a predetermined amount of the binding partner for the component to be determined when the component in said liquid sample and the component bound to said solid carrier have the same immunochemical properties;

d. contacting and incubating the reaction mixture with said enzyme-linked substance; and p1 e. determining the enzyme activity of substance bound to the solid phase, which is a measure of the presence and quantity of the component to be determined.]

[5. The method of claim 4 in which said hepatitis antigen is hepatitis B surface antigen, and the antibody is its associated antibody.]

[6. The method of claim 4 in which said solid carrier is washed after the incubation of the liquid sample with the immunological component bound to the solid carrier.]

[7. A diagnostic pack for the detection and determination of a component of an antigen-antibody reaction selected from the group consisting of an antigen and an antibody, consisting of:

a. one of said components coupled to a water-insoluble, water-insuspensible, solid carrier;

b. a substance having the same immunological properties as the component in (a) covalently linked to an enzyme; and c. the binding partner of the component to be determined if the component to be determined has the same immunological properties as the component in (a).]

[8. A diagnostic pack for the detection and determination of hepatitis B consisting of:

a. the antibody against Hepatitis B surface antigen coupled to a water-insoluble, water-insuspensible, solid carrier;

b. said antibody covalently linked to an enzyme; and c. Hepatitis B surface antigen in case the component to be determined is the antibody against Hepatitis antigen.]

*9. A method for the detection and determination of an antibody in a liquid sample containing said antibody to be detected and to be determined, comprising the steps of:*

*a. providing a given quantity of an antigen to said antibody, said antigen bound to the surface of a water-insoluble, water-insuspensible, solid carrier;*

*b. contacting and incubating a given quantity of said liquid sample having the antibody to be detected and determined with bound antigen of step (a), forming a reaction mixture having a solid phase and a liquid phase;*

*c. separating the solid phase from the liquid phase;*

*d. contacting and incubating with said solid phase a given quantity of a coupling product obtained by covalently binding a component having the same immunological properties as said antigen, to an enzyme, which quantity of coupling product is at least immunochemically equivalent to said antigen provided in step (a), in order to form a second solid phase and a second liquid phase; and*

*e. detecting and determining the enzyme activity of either the second solid or the second liquid phase of step (d) after separating the solid and liquid phases formed thereby, which detection and determination is a measure of the presence and quantity of said antibody to be detected and to be determined.*

*10. The method of claim 9, wherein the quantity of said bound antigen in step (a) is at least sufficient to react with all of the antibody to be determined.*

*11. The method of claim 9, wherein an additional step of separating the solid phase from the liquid phase takes place between steps (d) and (e).*

*12. The method of claim 11, wherein both separation steps are accomplished by washing the solid carrier.*

*13. A method for the detection and determination of a component of an antigen-antibody reaction in a liquid sample containing said component to be detected and determined, comprising the steps of:*

*a. providing a given quantity of a first reagent consisting of one component of said reaction selected from the group consisting of an antigen and an antibody bound to the surface of a water-insoluble, water-insuspensible, solid carrier with the proviso that said first reagent has the same immunochemical properties as the component to be detected and determined;*

*b. providing a predetermined amount of a binding partner for said first reagent, which amount is less than or is immunochemically equivalent to the given quantity provided in step (a) of the insolubilized component,*

*c. contacting and incubating a given quantity of said liquid sample having the component to be detected and determined with said reagents of step (a) and step (b), forming a reaction mixture having a solid phase and a liquid phase;*

*d. separating the solid phase from the liquid phase;*

*e. contacting and incubating with said solid phase a given quantity of a coupling product obtained by covalently binding a component having the same immunological properties as the first reagent, to an enzyme, which quantity of coupling product is at least immunochemically equivalent to the first reagent provided in step (a), in order to form a second solid phase and a second liquid phase; and*

*f. detecting and determining the enzyme activity of either the second solid phase or the second liquid phase of step (e) after separating the solid and liquid phases formed thereby, which detection and determination is a measure of the presence and quantity of the component to be detected and to be determined.*

*14. The method of claim 13, wherein said liquid sample and the binding partner of the component to be determined are preincubated with each other before contacting the sample with said solid carrier.*

*15. A method for the detection and determination of an antibody in a liquid sample containing the antibody to be detected and determined, comprising the steps of:*

*a. providing a given quantity of an antigen to said antibody, which antigen is bound to the surface of a water-insoluble, water-insuspensible, solid carrier;*

*b. contacting and incubating a given quantity of said liquid sample having said antibody to be detected and to be determined with said bound antigen of step (a), forming a reaction mixture having a solid phase and a liquid phase;*

*c. washing said solid carrier to separate the solid phase from the liquid phase;*

*d. contacting and incubating with said solid phase a given quantity of a coupling product, obtained by binding covalently a component having the same immunological properties as the antigen previously bound to the solid carrier, to an enzyme, which quantity of coupling product is at least immunochemically equivalent to said antigen provided in step (a) to form a second solid and second liquid phase;*

*e. washing the solid carrier to separate the solid phase from the liquid phase of step (d); and*

*f. detecting and determining the enzyme activity of the solid phase of step (d) after said washing, which detection and determination is a measure of the presence and quantity of said antibody to be detected and to be determined.*

*16. The method of claim 15, wherein said liquid sample and the binding partner of the antibody to be determined are preincubated with each other, before contacting the sample with said solid carrier.*

*17. A method for the detection and determination of a component of an antigen-antibody reaction in a liquid sample containing said component to be detected and determined, comprising the steps of:*

*a. providing a given quantity of a first reagent consisting of one component of said reaction selected from the group consisting of an antigen and an antibody, which component is bound to the surface of a water-insoluble, water-insuspensible, solid carrier, with the proviso that said first reagent has the same immunochemical properties as the component to be detected and determined;*

*b. providing a predetermined amount of a binding partner for the first reagent, which amount is less than or is immunochemically equivalent to the given quantity provided in step (a) of the insolubilized component,*

*c. contacting and incubating a given quantity of said liquid sample having the component to be detected and to be determined with said first reagent of step (a) and step (b), forming a reaction mixture having a solid phase and a liquid phase;*

*d. washing said solid carrier to separate the solid phase from the liquid phase;*

*e. contacting and incubating with said solid phase a given quantity of a coupling product, obtained by binding covalently a component having the same immunological properties as the component previously bound to the solid carrier, to an enzyme, which quantity of coupling product is at least immunochemically equivalent to the component of the first reagent provided in step (a) to form a second solid and second liquid phase;*

*f. washing the solid carrier to separate the solid phase from the liquid phase of step (e); and*

*g. detecting and determining the enzyme activity of the solid phase of step (e) after said washing, which detection and determination is a measure of the presence and quantity of the component to be detected and to be determined.*

*18. A method for the detection and determination of an antibody specific to an hepatitis antigen in a liquid sample containing said antibody, comprising the steps of:*

*a. providing a given quantity of an hepatitis antigen, which antigen is bound to a water-insoluble, water-insuspensible, solid carrier;*

*b. contacting and incubating said liquid sample having the antigen to be detected and determined with said bound antigen of (a) to form a reaction mixture;*

*c. separating the first solid phase from the first liquid phase;*

*d. contacting and incubating with said solid phase a given quantity of a coupling product obtained by covalently binding a component having the same immunological properties as the antigen bound to said carrier, to an enzyme, which quantity of coupling product is at least immunochemically equivalent to the first reagent provided in step (a) to form a second solid and second liquid phase;*

*e. contacting and incubating the reaction mixture to form a solid phase and a liquid phase; and*

*f. detecting and determing the enzyme activity of the solid phase of step (d) after separating the solid and liquid phases formed therein, which detection and determination is a measure of the presence and quantity of the antibody to be detected and determined.*

*19. The method of claim 18 in which said hepatitis antigen is hepatitis B surface antigen and the antibody is its associated antibody.*

*20. A method of the detection and determination of a component in the reaction of a hepatitis antigen and the associated antibody specific to said antigen in a liquid sample containing said component, comprising the steps of:*

*a. providing a given quantity of a first reagent consisting of one component of said reaction selected from the group consisting of said antigen and said antibody, which component is bound to a water-insoluble, water-insuspensible, solid carrier with the proviso that said first reagent has the same immunochemical properties as the component to be detected and determined;*

*b. providing a predetermined amount of a binding partner for the first reagent, which amount is less than or is immunochemically equivalent to the given quantity provided in step (a) of the insolubilized component;*

*c. contacting and incubating said liquid sample having the component to be detected and determined with said reagent of step (a) and step (b), to form a reaction mixture;*

*d. separating the first solid phase from the first liquid phase;*

*d. contacting and incubating with said solid phase a given quantity of a coupling product obtained by covalently binding a component having the same immunological properties as the component bound to said carrier, to an enzyme, which quantity of coupling product is at least immunochemically equivalent to the first reagent provided in step (a) to form a second solid and second liquid phase;*

*f. contacting and incubating the reaction mixture to form a solid phase and a liquid phase; and*

*g. detecting and determining the enzyme activity of the solid phase of step (e) after separating the solid and liquid phases formed therein, which detection and determination is a measure of the presence and quantity of the component to be detected and determined.*

*21. The method of claim 20 in which said hepatitis antigen is hepatitis B surface antigen and the antibody is its associated antibody.*

*22. A diagnostic pack for the detection and determination of a component of an antigen-antibody reaction selected from the group consisting of an antigen and an antibody, consisting of:*

*a. a given quantity of a first reagent consisting of one component of said reaction selected from the group consisting of an antigen and an antibody bound to the surface of a water-insoluble, water-insuspensible, solid carrier;*

*b. a given quantity of a coupling product obtained by covalently binding a component having the same immunological properties as the component in (a) to an enzyme, which quantity of coupling product is at least immunochemically equivalent to the component of the first reagent provided in (a); and* c. a predetermined amount of a binding partner of the first reagent, which amount is less than or is immunochemically equivalent to the given quantity (*a*) *of the insolubilized component.*

*23. A diagnostic pack for the detection and determination of an antibody, consisting of:*

*a. a given quantity of an antigen bound to the surface of a water-insoluble, water-insuspensible, solid carrier; and*

*b. a given quantity of an antigen having the same immunological properties as the antigen in (a) coupled to an enzyme, which quantity of antigen is at least immunochemically equivalent to said antigen provided in (a).*

*24. A diagnostic pack for the detection and determination of antibody directed against hepatitis B, consisting of:*

*a. a given quantity of hepatitis B surface antigen coupled to a water-insoluble, water-insuspensible, solid carrier; and*

*b. a given quantity of a coupling product obtained by covalently binding hepatitis B surface antigen to an enzyme, which quantity is at least immunochemically equivalent to the antigen in (a).*

* * * * *

UNITED STATES PATENT AND TRADEMARK OFFICE

CERTIFICATE OF CORRECTION

PATENT NO. : Re. 32,696

DATED : Jun. 14, 1988

INVENTOR(S) : Antonius H. W. M. Schuurs, Bauke K. Van Weemen and Gerrit Wolters

It is certified that error appears in the above-identified patent and that said Letters Patent is hereby corrected as shown below:

On the title page, in item [45], "Reissued Date of Patent: Jun. 14, 1988" should read --Reissued Date of Patent: * Jun. 14, 1988--.

On the title page, insert the following:

--[*] Notice: The portion of the term of this patent subsequent to February 12, 1991 has been disclaimed.--

Signed and Sealed this

Eleventh Day of August, 1992

*Attest:*

DOUGLAS B. COMER

*Attesting Officer*

*Acting Commissioner of Patents and Trademarks*